United States Patent
Nunokawa et al.

(10) Patent No.: US 6,951,734 B2
(45) Date of Patent: Oct. 4, 2005

(54) METHODS FOR PRODUCING PROTEINS BY USING CELL-FREE PROTEIN SYNTHESIS SYSTEMS

(75) Inventors: Emi Nunokawa, Kanagawa (JP); Takanori Kigawa, Kanagawa (JP); Takashi Yabuki, Kanagawa (JP); Shigeyuki Yokoyama, Kanagawa (JP)

(73) Assignee: Riken, Saitama (JP)

( * ) Notice: Subject to any disclaimer, the term of this patent is extended or adjusted under 35 U.S.C. 154(b) by 280 days.

(21) Appl. No.: 09/989,974

(22) Filed: Nov. 20, 2001

(65) Prior Publication Data

US 2002/0168705 A1 Nov. 14, 2002

(30) Foreign Application Priority Data

Mar. 8, 2001 (JP) ........................................ 2001-065799

(51) Int. Cl.[7] .......................... C12P 21/06; C12Q 1/00; C09F 1/00
(52) U.S. Cl. .................. 435/68.1; 435/4; 435/69.1; 435/69.9; 435/71.1; 435/71.2; 530/219; 530/224; 530/333; 530/417
(58) Field of Search .................. 435/68.1, 4, 69.1, 435/69.9, 71.1, 71.2; 530/219, 224, 333, 417

(56) References Cited

FOREIGN PATENT DOCUMENTS

| EP | 1143009 | 10/2001 |
|---|---|---|
| JP | A-4-200390 | 7/1992 |
| JP | A-2000-175695 | * 6/2000 |

OTHER PUBLICATIONS

Sprin wt al., Science, vol. 242, pp. 1162–1164, Nov. 25, 1988.*

Hendrickson. Science, vol. 254, pp. 51–58, Oct. 4, 1991.*

Hendrickson. "Determination of Macromolecular Structures from Anomalous Diffraction of Synchrotron Radiation" Science 254:51–58 (1991).

Kigawa et al. "Structure Determination of Protein Folds Using the Cell–free Synthesis and NMR Spectroscopy" Experimental Medicine 18(18):60–64 (2000).

Spirin et al. "A Continuous Cell–Free Translation System Capable of Producing Polypeptides in High Yield" Science 242:1162–1164 (1988).

* cited by examiner

*Primary Examiner*—Jon Weber
*Assistant Examiner*—Abdel A. Mohamed
(74) *Attorney, Agent, or Firm*—Morrison & Foerster LLP

(57) ABSTRACT

A method for producing a protein suitable for X-ray crystallographic analysis, in a cell-free protein synthesis system comprising a cell-free extract, a nucleic acid coding for said protein, and amino acids for the substrate of said protein, wherein said amino acids comprises at least one amino acid comprising a heavy atom, and wherein the introduced rate of said amino acid comprising the heavy atom into the synthesized protein is at least 80%.

14 Claims, 5 Drawing Sheets

Ras-GDP (Cell-free)

Ras-GDP (*in vivo*)

A. M. deVos *et al.* (1988)

METHODS FOR PRODUCING PROTEINS BY USING CELL-FREE PROTEIN SYNTHESIS SYSTEMS

RELATED APPLICATIONS

This application claims priority to Japanese Patent Application No. 2001-065799 filed on Mar. 8, 2001.

FIELD OF THE INVENTION

The present invention relates to a method for producing a protein by using a cell-free protein synthesis system comprising a cell extract, and in particular to a method for producing a protein suitable for X-ray crystallographic analysis.

BACKGROUND OF THE INVENTION

Recently, DNA sequences of various species have been determined rapidly, and "structural genomics" is recognized as an important research. With respect to a large number of genes selected from a mass of information about genomic sequences, structural genomics aims the systematic determination of three dimensional structures of proteins coded on each gene, and the comprehensive study of the structure/function relationships.

In the research of structural genomics, many types of proteins which are from 30,000 to more than 40,000 in case of human's proteins, can be targets of structural analysis. Therefore, it is necessary to select the target proteins efficiently. At the same time, actual expressions and preparations of the selected targets are required for the large-scale preparation of samples necessary for structural analysis on a milligram scale.

In the past, for the preparation of such samples, the gene engineering methods in which cloned DNAs are introduced into living cells such as *E. coli* cell have been generally used. However, these kinds of methods can be applied only in the case where exogenous proteins are restricted to molecular species that can pass through the life-support mechanisms of the host cell. On the other hand, the progress in chemical synthesis technology has made it possible to produce peptides consisting of several tens of amino acids automatically. But, limitations of the yield, the secondary reactions, and other factors make it very difficult to produce proteins with large molecular weights.

As for methods for analyzing the three dimensional structural of proteins, X-ray crystallography has been usually used. The recent use of the synchrotron beam has allowed generation of stronger X-rays (compared with other X-ray generators) in addition to allowing a selection of any wavelength. As a result, even in the case where there is only a kind of heavy atom in the proteins, it has become possible to determine three dimensional structures by the use of MAD (multiwavelength anomalous diffraction) method (Hendrickson, W. A., Science, 254, 51–58 (1991)). One benefit MAD provides is that it reduces the time it takes to determine three dimensional structures of proteins.

In case of the determinations of the three dimensional structures of proteins by the use of X-ray crystallography, preparations of heavy atom isomorphous replacement product of the proteins are necessary for determination of the phase, and, in many cases, proteins containing selenomethionine are used as the said heavy atom isomorphous replacement product. Uses of selenomethionine instead of methionine and expressions of the genes in methionine-requiring auxotrophic mutant strains make it possible to introduce selenium into the proteins.

However, expression systems using living cells have the problems that, because of cytotoxicity of selenomethionine, the expression levels of proteins are very low and sufficient substitution rates of selenomethionine cannot be achieved.

To solve these problems, as a protein synthesis method which harmonizes the biological method with the chemical method, and fully utilizes excellent features of organisms, developments of a cell-free protein synthesis system to produce proteins in vitro by using a cell extract are in progress (for example, Science (1988) 242, 1162–1164, JP Patent Kokai Publication JP-A-4-200390). This cell-free protein synthesis system provides that organic translation systems of genetic information are assorted in artificial chambers, and that synthetic systems are reconstructed in order to introduce any amino acids including non-natural types, by the use of designed nucleic acids as templates.

Because the cell-free protein synthesis system requires complicated and multi step manipulations, and because the productivities were very low in the past, the applications of the cell-free protein synthesis systems were limited. A synthesis system (JP Patent Kokai Publication JP-A-2000-175695) using dialysis has led to the practical application of this technology.

However, the problems in the art have not been overcome yet. In case of the synthesis of heavy atom isomorphous replacement product, preparations of materials for protein synthesis and establishment of the best conditions are complicated and difficult. Additionally, there are no reports that X-ray crystallography of proteins produced by the cell free protein synthesis system has been achieved by the use of the MAD method. Therefore, the introduced rates of heavy atoms to proteins has not been considered sufficiently efficient yet.

SUMMARY OF THE INVENTION

The present invention relates to providing quick and easy methods of synthesis of heavy atom isomorphous replacement product proteins suitable for X-ray crystallography, especially for the phase determination by the MAD method.

The present inventors have researched the methods to introduce heavy atoms into proteins for X-ray crystallography. As a result, for the cell-free protein synthesis system using cell extract, the optimization of various conditions make it possible to produce high concentrations of proteins introduced with heavy atoms at high introduced rates ("rates of introduction"). Furthermore, the X-ray crystallography of crystal of the proteins produced by the method was found to make rapid and accurate determinations of the three dimensional structures. These findings have led to the following inventions.

According to a first aspect of the present invention, there is provided a method for producing a protein suitable for X-ray crystallographic analysis, by synthesizing a protein using a cell-free protein synthesis system comprising a cell extract, a nucleic acid coding for said protein, and amino acids for the substrate of said protein, wherein said amino acids comprise at least one amino acid comprising a heavy atom, and wherein the introduced rate of said amino acid comprising the heavy atom into the synthesized protein is at least 80%.

In preferred embodiments of the present invention, said cell-free protein synthesis system consists essentially of an internal dialysate and an external dialysate through a dialysis membrane. The internal dialysate comprises said cell extract and said nucleic acid coding for the protein, and the internal dialysate and/or the external dialysate comprise said amino acids for the substrate of said protein. It is preferable that said cell extract is prepared from E. coli, thermophilic bacteria, or yeast. Furthermore, it is more preferable that said E. coli cell extract is prepared by concentrating E. coli S30 cell extract fraction.

In more preferred embodiments of the present invention, said external dialysate further comprises an ATP regenerating system, a high-molecular weight absorbent, and a reducing agent, and, is exchangeable for a fresh external dialysate, or additional portion thereof, when the production rate of the synthesized protein is reduced. And, it is preferable that a cutoff molecular weight of said dialysis membrane range from 10,000 Da to 100,000 Da. A combination of creatine kinase and creatine phosphate is included as the ATP regenerating system.

As a heavy atom introduced by the methods of the present invention, mercury, platinum, iodine, iron, and selenium are included. And, as an amino acid comprising such heavy atoms, an amino acid such as selenomethionine or selenocysteine can be suitably used.

According to another aspect of the present invention, there is provided a protein produced by said methods wherein said introduced rate of said amino acid comprising the heavy atom is at least 95%.

DETAILED DESCRIPTION OF THE INVENTION

Figure 1:
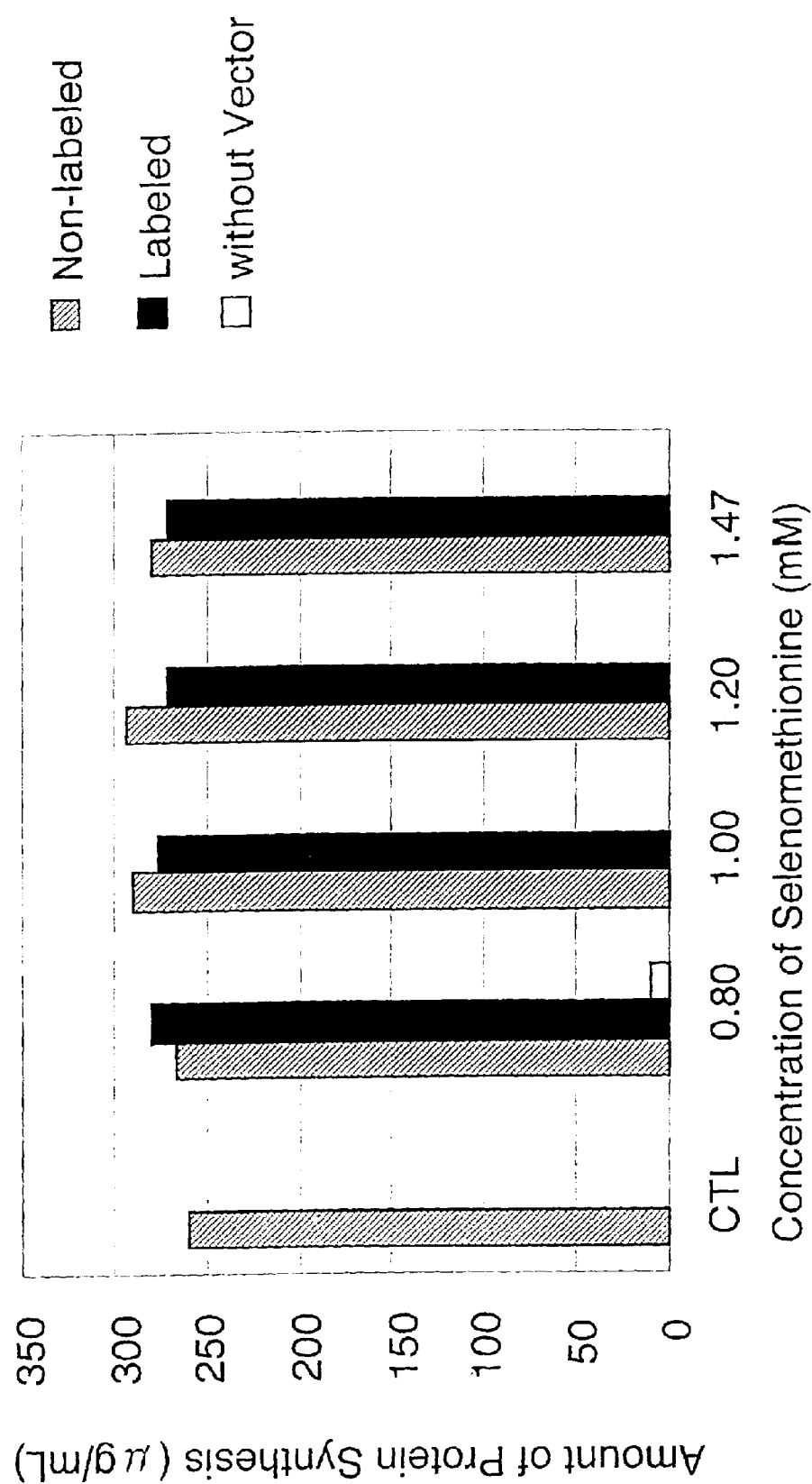
FIG. 1 shows the relationship between concentrations of selenomethionine added to internal and external dialysate in the cell-free protein synthesis system and the yield of protein (amount of protein synthesis).

In the present invention, the cell-free protein synthesis system is a in vitro protein synthesis system using a cell extract. The system may be either a cell-free translation system for producing proteins on ribosome through reading of information of mRNA, or a system in which a cell-free transcription system produces mRNA using DNA as the template and mRNA information are translated into proteins.

As cell extract, eukaryotic or prokaryotic cell extract containing factors required for protein synthesis such as ribosome, tRNA, and so forth can be used. As eukaryotic or prokaryotic cell, any of generally known cells can be used. For example, E. coli, thermophilic bacteria, wheat germ, rabbit reticulocyte, murine L-cell, Ehrlich ascitic cancer cell, HeLa cell, CHO cell, and budding yeast can be used. Especially, E. coli cell extract (for example, E. coli S30 cell extract fraction) or Thermus thermophilus cell extract is desirable for the high yield. The E. coli S30 cell extract fraction can be prepared from E. coli A19 strain (rna, met), BL21 strain, BL21 star strain, BL21 codon plus strain, and so forth in accordance with generally known methods (Pratt, J. M. et al., transcription and translation—a practical approach, (1984), pp. 179–209, Henes, B. D. and Higgins, S. J. eds., IRL Press, Oxford), or can be purchased (from companies such as Promega or Novagen).

Either each concentrated extract of the cell extract (hereinafter referred to as "concentrated cell extract") or each non-concentrated one (hereinafter referred to as "crude cell extract") can be used as a cell extract. However, in the case of concentrated cell extract, higher yield of proteins can be achieved. To prepare the concentrated cell extract, any method such as ultrafiltration, dialysis, PEG precipitation, and so forth can be used. The degree of the concentration is usually not less than one and a half times, desirably not less than two times. In case of E. coli cell extract, it is possible by the use of ultrafiltration centrifugation to concentrate the extract from one and a half times to not less than seven times, and PEG precipitation makes it possible to concentrate the extract from one and a half times to not less than five times. However, in the case where the degree is over four times, the handling becomes difficult. In the case of wheat germ cell extract, it is possible, by the use of PEG precipitation, to concentrate the extract over ten times (Nakano, H. et al., supra). In case of the PEG precipitation method, by addition of PEG solution to the cell extract, the proteins and the nucleic acid are precipitated and collected. And, the precipitation is dissolved in a small amount of buffer solution to prepare the concentrated cell extract. Concentration by dialysis can be achieved, for example, in a closed system which can be shaken or stirred. In the system, internal dialysate of cell extract is dialyzed to external dialysate through a dialysis membrane (For example, the cutoff molecular weights range from 1000 Da to 14,000 Da.). As for the system, the external dialysate can use buffer solution containing potassium acetate, magnesium acetate, and dithiothreitol, and can also use high-molecular weight (polymer) absorbents such as PEG (for example, #8000) or sucrose/epichlorohydrin water-soluble synthetic copolymer (for example, SIGMA Ficoll). The high-molecular weight (polymer) absorbent is essential to absorb moisture from the internal dialysate into the external dialysate through the dialysis membrane.

As for the methods of the present invention, use of the dialysis method is preferable. However, in addition to this method (or in conjunction therewith), for example, a batch method and a flow method may also be used. Said dialysis method is a method in that protein synthesis system comprising the cell extract is used as the internal dialysate, and the internal dialysate is dialyzed to the substrates of protein synthesis involved in the external dialysate through the dialysis membrane which makes material transfer possible. The produced proteins can be collected from the internal or external dialysate.

In addition to the concentrated cell extract (10 to 90 weight %) such as the E. coli S30 fraction, the internal dialysate may contain DNA or RNA (MRNA and the like) coding for the objective proteins, ATP (0.5 to 5 mM), GTP (0.05 to 1.0 mM), CTP (0.05 to 1.0 mM), UTP (0.05 to 1.0 mM), buffer solutions, salts, amino acids, RNase inhibitors, antibacterial agents, RNA polymerase if necessary (in case where DNA is used as template), and tRNA. In addition, it can contain ATP regenerating systems, polyethyleneglycol (for example, PDG#8000), 3', 5'-cAMP, folic acids (0.1 to 5 mM), reducing agents (for example, 1 to 19 mM dithiothreitol). On the other hand, the external dialysate can use the same composition of said internal dialysate excluding cell extract, RNase inhibitors, DNA or RNA, and RNA polymerase.

For the buffer solution, for example, buffer agent such as Hepes-KOH or Tris-OAc can be used. For salts, acetate (for example, ammonium salts, magnesium salts, and the like) or glutamate salts can be used. For antibacterial agents, sodium azide or ampicillin can be used. In case where DNA is used for the template, RNA polymerase is added to the reaction system, and enzymes on the market such as, for example, T7 RNA polymerase can be used.

In the present invention, a combination of 0.02 to 5 μg/μL of creatine kinase (CK) and 10 to 100 mM of creatine phosphate (CP) is preferably used as the ATP regenerating system, but is not limited only to this system. Any material which is known in the prior art can be used. In addition to the combination described above, a combination of 1 to 20 mM of phosphoenolpyruvate (PEP) and 0.01 to 1 μg/μL of pyruvate kinase (PK) also can be used. PK and CK are enzymes which regenerate ADP to ATP, and require PEP and CP as the substrate respectively.

Proteins produced by the present invention may be any known and/or novel protein. Either DNA or RNA can be used as the nucleic acid coding for objective proteins, and can be extracted from eukaryotic or prokaryotic cells or tissues. DNA cloned from cDNA and others by known methods can also be used. Moreover, because DNA fragments amplified by PCR methods using the extracted DNA, cDNA, or genomic library as the template can be used directly, simultaneous and rapid expressions and preparations of many proteins can be done without complicated operations of cloning to expression vectors required previously.

On operations of the present invention, the internal dialysate is put inside the dialysis membrane, and the external dialysate is put outside the membrane. By shaking or stirring of the closed system where materials can transfer through the membrane in dependence on the cutoff molecular weight, produced objective proteins can be collected from the internal or external dialysate. For the reaction conditions such as temperature, stirring condition, and so forth, any condition can be used in dependence of the kind of proteins. For example, the reaction temperature is usually from 25 to 50° C., preferably 37° C. However, the temperature of synthesis system using *Thermus thermophilus* cell-free extract can be over 50° C.

It is desirable to exchange the external dialysate for a fresh external dialysate, or an additional portion thereof, when the reaction rate is found to be reduced. Moreover, usage of a dialysis membrane with a cutoff molecular weight of more than 10,000 Da, preferably more than approximately 50,000 Da, can make the output of the proteins higher.

According to the invention, one or more of the amino acids, comprising a heavy atom, are added with the cell extract to the cell-free protein synthesis system. The amino acids include the 20 kinds of amino acids which construct proteins, and it is sufficient that at least a kind of these amino acids comprises a heavy atom. As said heavy atom, any atom which induce anomalous scattering of X-ray can be used, and mercury (Hg), platinum (Pt), iodine (I), iron (Fe), or selenium (Se) are normally used. Especially for production of proteins suitable for the MAD method, mercury (Hg), selenium (Se), and iron (Fe) are effective. As the amino acids comprising a heavy atom, the 20 kinds of any amino acids constituting proteins or their analogs may be used. With reference to the easiness of treatment and manufacturing method, it is desirable to use selenomethionine or selenocysteine. These amino acids comprising selenium can be made easily by substitution of intramolecular sulfur (S) atoms to selenium (Se) atoms.

According to one embodiment of the present invention, selenomethionine instead of methionine is added to the internal and/or external dialysate. The amount of addition is usually 0.5 to 3.0 mM of the concentration, desirably 0.8 to 1.5 mM of the concentration.

By crystallization of such a protein introducing a heavy atom, it is possible to prepare a crystal which has the same arrangement of protein molecules compared with the native crystal, and whose difference is only the addition of a heavy atom, that is, the heavy atom isomorphous replacement crystal. The heavy atom isomorphous replacement crystal is important for determinations of phases on X-ray crystallography. Especially in the case of phase determination utilizing anomalous scattering, the phase determination can be easily done without preparations of the plural heavy atom isomorphous replacement crystal.

The introduction rates of the amino acid comprising a heavy atom to the protein produced by the methods of the present invention are slightly different according to the kind of objective proteins and the kind of amino acid comprising a heavy atom. However, the rate can be usually at least 80%, desirably at least 90%, and more preferably at least 95%. Here, "introduced rate," for example, in case of using selenomethionine as the amino acid comprising heavy atoms, indicate a substitution ratio of selenomethionine for methionine in the protein molecule. The rate can be analyzed by generally known methods such as mass spectrometry and/or amino acid composition analysis. For homogeneity of the heavy atom isomorphous replacement crystal to acquire better X-ray diffraction data, it is to be desired that the introduction rate of heavy atoms is almost 100%.

Since the quantity and the number of kinds of mixed contaminants are extremely small, compared with the isolations from living cells, purifications of the produced proteins can be achieved relatively easily. Depending on the properties of the proteins, each of the generally known methods of purification can be used individually or, if necessary, can combined together. For example, conventional techniques of ammonium sulfate or acetone precipitation, acid extraction, anion or cation exchange chromatography, hydrophobic interaction chromatography, affinity chromatography, gel filtration chromatography, HPLC, electrophoresis, chromatofocusing, and the like can be used. Identifications and quantitative determinations of produced proteins can be achieved by activity assays, immunological assays, spectroscopic measurements, amino acid analyses, and the like, if necessary, comparing with standard samples.

The crystallization of purified proteins can be achieved by the generally known method that solubility of the objective proteins is reduced gradually to the concentration of saturated solution. As such methods, dialysis, vapour-diffusion method, batch method, free-interface diffusion method, concentration method, temperature gradient method, and the like can be used. For example, the vapour-diffusion method has a mechanism that, through vapor phase, volatile solvents and precipitants are transferred by diffusion. Vapour-diffusion between protein solution and precipitant solution increases concentrations of protein and precipitant simultaneously, and induces the crystallization in the supersaturated area. As for the preparation method of drops of protein solution, there are the hanging-drop method, the sitting-drop method, the sandwiches method, and the like may be used.

For the precipitant for crystallization, salts such as ammonium sulfate (($NH_4$)$_2SO_4$), sodium sulfate ($Na_2SO_4$), lithium chloride (LiCl), and sodium phosphate ($Na_2PO_4$), or organic compounds such as methanol, ethanol, and polyethyleneglycol may be used. The condition for crystallization is determined in consideration of various terms such as kind and concentration of the precipitant, and/or temperature and pH of the protein solution.

The X-ray crystallography includes the multiwavelength anomalous diffraction (MAD) method. The X-ray used in this method can be obtained from synchrotron radiation, and the wavelength is 0.3 to 3.0 angstroms. The MAD method is a way to get X-ray diffraction data of plural wavelengths from the heavy atom isomorphous replacement crystal which has the absorption edge near the energy of incoming X-rays. Resonance between the X-ray and electron shell of the objective heavy atom induces differences among X-ray diffractions, and problems of the phase on the structural analyses of protein can be solved by this. The theory behind this method has been known for a long time. However, the method has not been able to apply to determination of protein structures until the advent of synchrotron radiation with variable wavelengths. By this method, Hendrickson and his group succeeded in analyzing protein structures for the first time (Hendrickson W. A. et al., Proteins 4, 77–88. (1988); Hendrickson W. A. et al., EMBO J., 5, 1665–1672. (1990)).

The synchrotron radiation is a radiation which can be obtained by acceleration through a magnetic field of electrons shot into a storage ring, which provides relatively greater energy than that produced by usual X-ray generators. Third-generation large-scale synchrotron radiation facilities SPring-8 (8 GeV) at Institute of Physical and Chemical Research (RIKEN) can be used.

EXAMPLES

The present invention is explained in more detail by reference to the following examples using Ras protein, an oncogene product. Ras protein is a protein whose three dimensional structure has been already determined, however, it does not restrict the scope of the present invention.

Example 1

Synthesis of Selenomethionine Introduced Ras Protein by the Cell Free Protein Synthesis Method Using *E. coli* S30 Extract

*E. coli* S30 extract was prepared from *E. coli* BL21 codon plus strain in accordance with the method of Zubay et al. (Annu. Rev. Geneti., 7, 267–287 (1973)).

13 μg of pK7-Ras (Kigawa et al., J. Biomol. NMR, 6, 129–134. (1995)) which is an expression vector for Ras protein was added to 2.1 mL of the protein synthesis reaction mixture (internal dialysate) whose composition is shown in the following Table 1. And, 0.9 mL of the said *E. coli* S30 cell extract was added to start the protein synthesis reaction.

TABLE 1

Composition of protein synthesis reaction mixture (internal dialysate)

| Composition | Concentration |
| --- | --- |
| Hepes-KOH (pH 7.5) | 58 mM |
| DTT | 2.7–2.8 mM |
| ATP | 1.2 mM |
| GTP | 0.87 mM |
| CTP | 0.87 mM |
| UTP | 0.87 mM |
| L-(-)-5--5,6,7,8-tetrahydrofolate | 35 μg/mL |
| cyclic AMP(cAMP) | 0.64 mM |
| Ammonium acetate | 28 mM |
| Potassium glutamate | 200 mM |
| Polyethylene glycol 8000(PEG8000) | 4.0% (w/v) |
| Creatine phosphate | 81 mM |
| Magnesium acetate | 11 mM |
| 19 kinds of amino acid other than methionine | Each 1 mM |
| Selenomethionine | 1 mM |
| Sodium azide | 0.05% |
| Creatine kinase | 0.25 μg/mL |
| T7 RNA polymerase | 0.27 mg/mL |
| RNase inhibitor (Toyobo) | 0.5 U/mL |

Composition of materials for the protein synthesis (external dialysate) was the same as shown in the above Table 1 excluding creatine kinase, T7 RNA polymerase, and RNase inhibitor.

As for the amount of added selenomethionine, a system using, instead of pK7-Ras which is an expression vector of the Ras protein, pK7-CAT carrying CAT gene (CAT expression vector; Kim et al., Eur. J. Biochem., 239, 881–886. (1996)) was used to determine the optimum amount by changing the concentration of selenomethionine. The result is shown in FIG. 1. Quantitative determination of the produced CAT protein was achieved in accordance with the method of Shaw et al. (Methods Enzymol. 735–755. (1975)). This result showed that yield of CAT protein was little affected by existence of selenomethionine label, and that about 1.00 mM of the addition was sufficient.

To synthesize Ras protein, 30 mL of the external dialysate was used to 3 mL of the internal dialysate, and the dialysis was done at 37° C. for six hours with Spectra/Por 7 (Spectrum). After the synthetic reaction, the synthesized protein was purified by anion exchange chromatography (Source 15 Q) and gel filtration chromatography (Superdex 75), and purity of the protein was tested by SDS polyacrylamide gel electrophoresis (SDS-PAGE). As a result, an almost single band was detected on the SDS-PAGE.

Furthermore, to determine the introduced rate of selenomethionine, mass spectrometry of the purified protein was achieved by the LC-MAS method.

Figure 2:
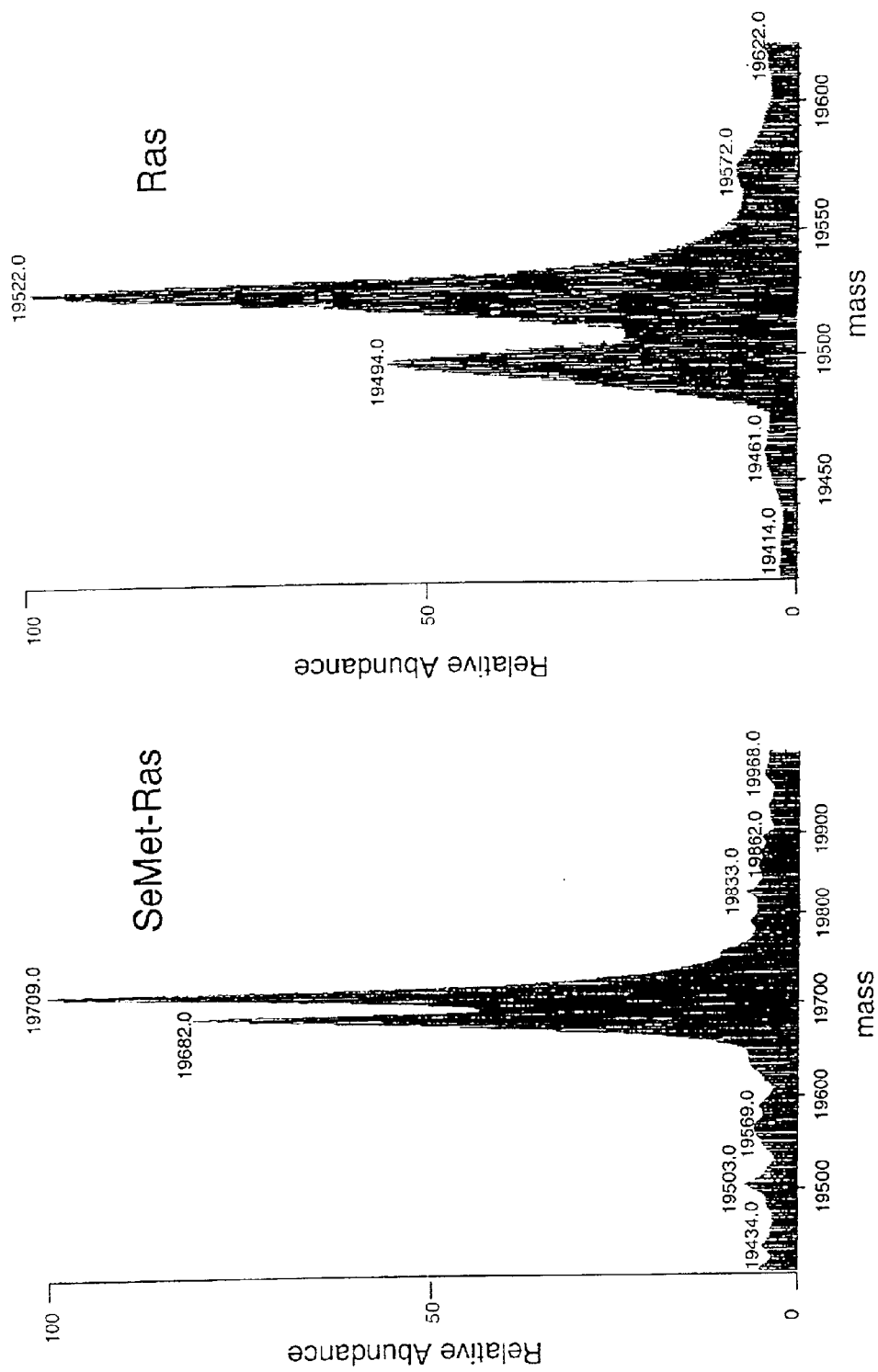
FIG. 2 shows the analytical results of mass spectrometry for Ras proteins synthesized using the cell-free protein synthesis system, (a) selenomethionine introduced Ras protein, (b) Ras protein without selenomethionine.

In FIG. 2, results of measurements for the selenomethionine introduced Ras protein obtained by the aforementioned method and those for Ras protein without selenomethionine are shown. There are 2 kinds of Ras proteins. One is N-terminal formylated form, and the other is non formylated form. Two peaks of different molecular weights (19,494.0 Da and 19,522.0 Da) can be seen respectively (FIG. 2(*b*)). Because Ras protein has four methionine residues, there is a possibility that the plural peaks of different molecular weights are detected if the number of introduced methionine is not constant. However, as shown in FIG. 2(*a*), even on the results of measurements for the selenomethionine introduced Ras protein, only two peaks arose from the existence of the formylation were detected. Furthermore, the increase in the molecular weights (19,662.0 Da and 19,709.0 Da) suggests that all of the four sulfur atoms are completely substituted for selenium atoms, namely, all of four methionine residues are completely substituted for selenomethionines. The result indicates that, even if considering measurement errors of the mass spectrometry, at least not less than 95% of methionine residues of Ras protein are substituted for selenomethionines, namely, the introduced rate of selenomethionine is at least not less than 95%.

Example 2

Crystallization of Selenomethionine Introduced Ras Protein

Figure 3:
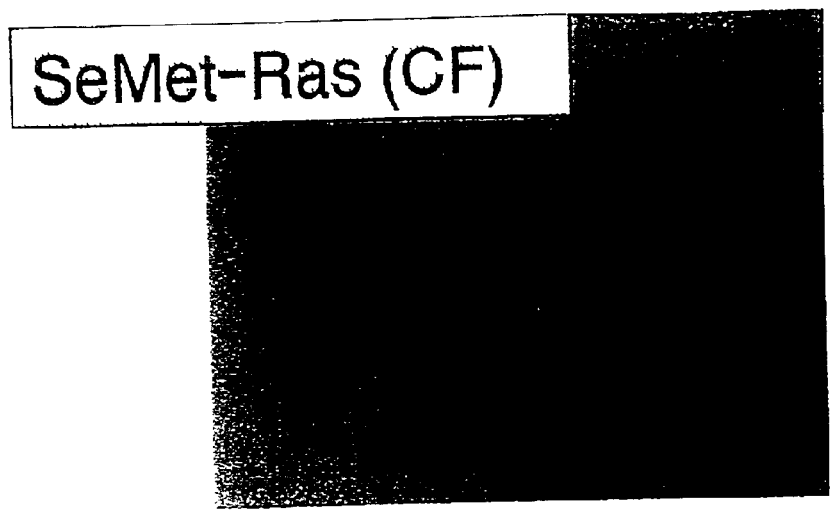
FIG. 3 shows photographs of crystals of Ras proteins crystallized under various conditions.
Figure 3:
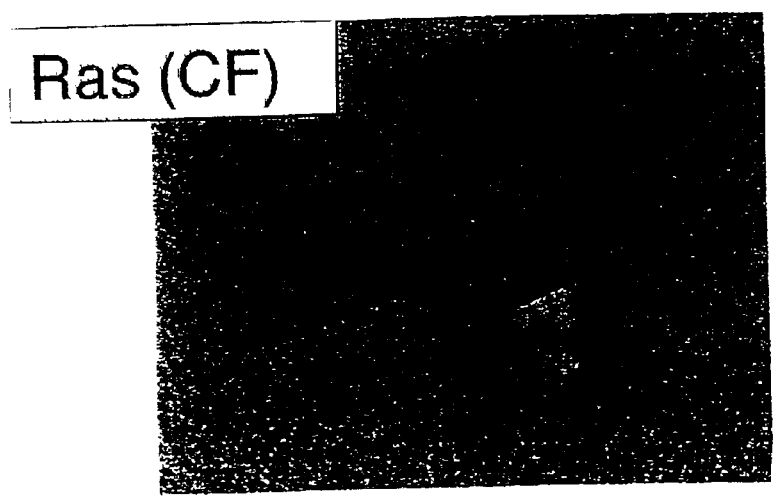
Figure 3:
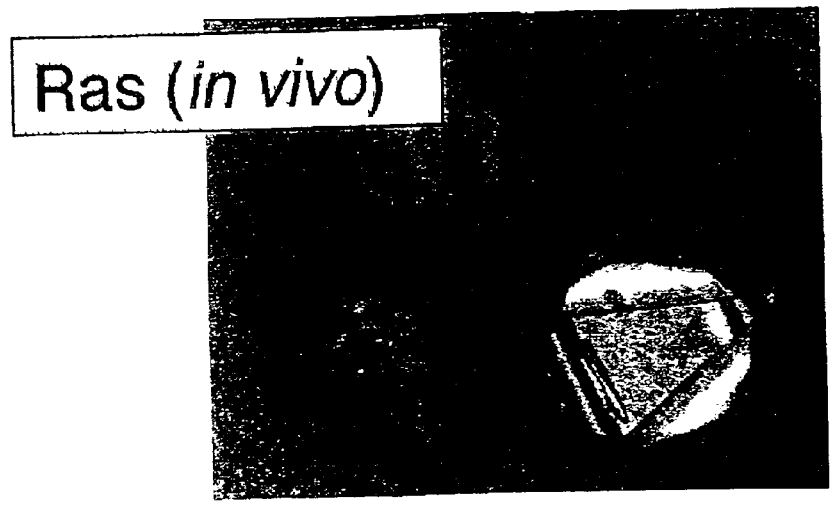

To crystallize the selenomethionine introduced Ras protein by hanging drop vapor diffusion method, the proteins purified by the method of Example 1 were dissolved in solution comprising 0.2M of calcium acetate, 0.1M of sodium cacodylate (pH6.5), and 18% of PEG8000. The crystal shown in FIG. 3 was formed through letting the said protein solution stand with solution comprising 0.2M of calcium acetate, 0.1M of sodium cacodylate (pH6.5), and 18% of PEG8000 at 37° C. for two days in a hermetically sealed chamber by hanging drop vapor diffusion method.

Example 3

Figure 4:
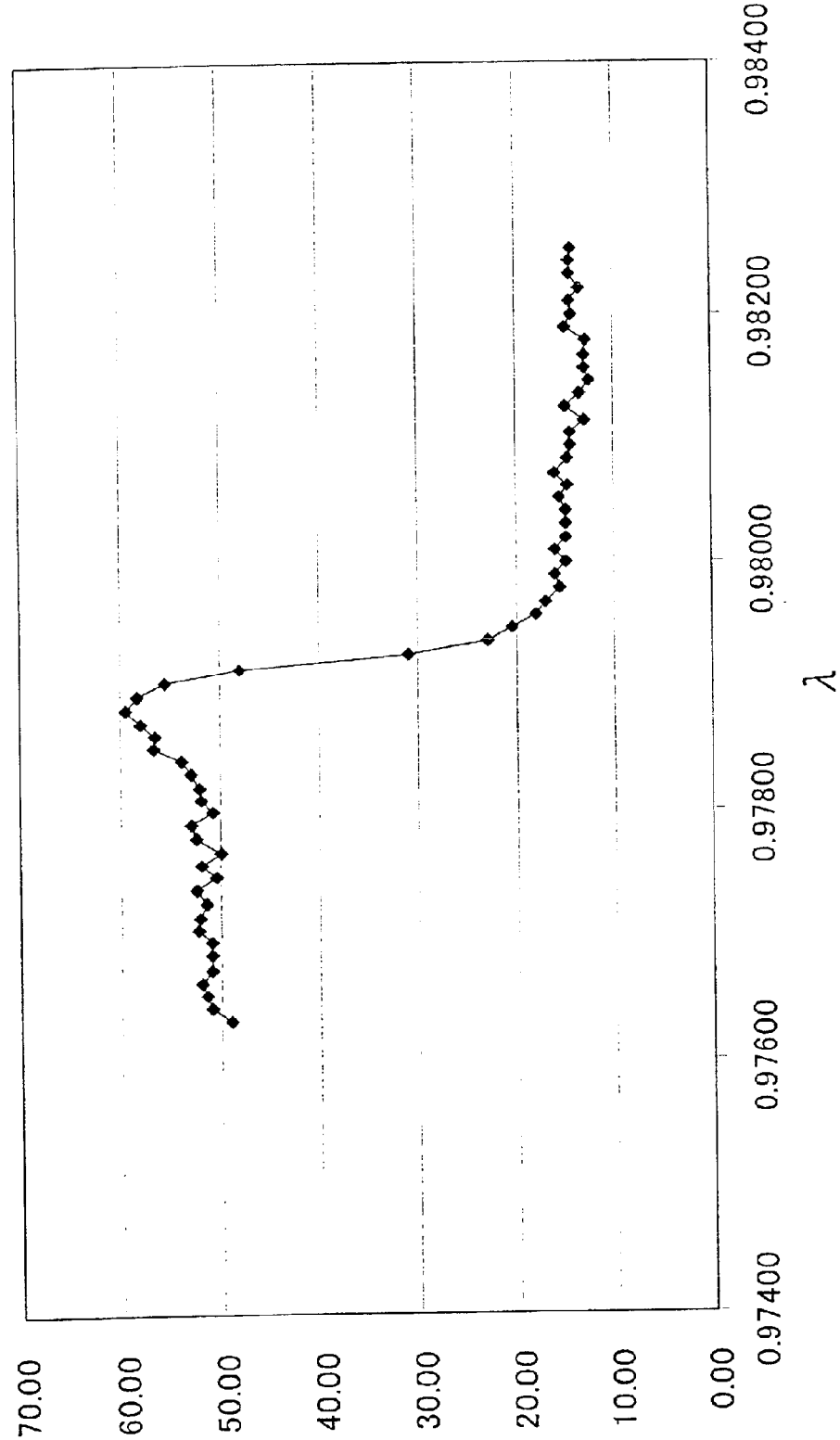
FIG. 4 shows the result of measurement of the X-ray absorption fine structure (XAFS) of crystal of selenomethionine introduced Ras protein.

The Three Dimensional Structural Analyses of Ras Protein by X-Ray Crystallography Using crystal prepared in example 2, the X-ray crystallography was achieved with beamline (BL44B2) of the large-scale synchrotron radiation facilities SPring-8 (8 GeV) at Institute of Physical and Chemical Research (RIKEN). FIG. 4 shows the chemical bound state of selenium atoms in Ras protein solved by measurement of the X-ray absorption fine structure. From this result, it can be understood that an absorption of X-ray is seen at the selenium specific wavelength, and that the wavelength measured by MAD method can be estimated.

On the basis of the data of X-ray absorption fine structure, data by multiwavelength anomalous diffraction (MAD) method were acquired at 4 kinds of wavelength (0.979251 angstroms, 0.978815 angstroms, 0.971148 angstroms, and 0.986604 angstroms). Determinations of the phases and drawing of the electron density map were made with DENZO/SCALEPACK program (Otwinowski, Z. and Minor, W., Macromol. Crystallorg., A276, 307–326. (1997)), SHARP program (de la Fortelle, E., Irwin, J. J., and Bricogne, G. Crystallogr. Comput., 7, 1–9 (1997)), Shake-and-Bake program (Miller, R., DeTitra, G. T., Jones, R., Langs, D. A., Weeks, C. M., and Hauptman, H. A., Science, 259, 1430–1433 (1993)), SOLOMON program (Collaborative Computational Project Number 4, Acta Crystallorg., D50, 760–763. (1994)), O program (Jones, T. A., Zou, J. Y., Cowan, S. W., and Kjeldgaard, Acta Crystallogr., A47, 110–119. (1991)), and CNS program (Brunger, A. T., et al., Acta Crystallogr., D54, 905–921. (1998)). These results are shown in Table 2 and 3. Table 2 indicates that the crystal of Ras protein labeled with selenomethionine in Example 3 (SeMet-Ras (CF)) shows the same space group and lattice constant as both of the crystal of proteins synthesized without selenomethionine in $E.$ $coli$ living cells (Ras (in vivo)) and the crystal of proteins synthesized without selenomethionine labeling by the cell free protein synthesis system (Ras (CF)) show, and that all of them have the same three dimensional structure. In Table 3, phase data at the four wavelengths measured by the MAD method are shown.

TABLE 2

Comparison of X-ray crystallographic data from different methods for protein synthesis.

| | Ras (in vivo) | Ras (CF) | SeMet-Ras (CF) |
|---|---|---|---|
| Space group | P6522 | P6522 | P6522 |
| Lattice constant A = B | 83 | 83 | 83 |
| Lattice constant C | 103 | 103 | 103 |
| R-sym | 0 | 0 | 0 |
| (2.02–2.00) | 0 | 0 | 0 |
| Completeness (%) | 1 | 1 | 1 |
| (2.02–2.00) | 1 | 1 | 1 |
| Multiprisity(a/b) | 15 | 16 | 19 |
| Unique reflections(a) | 14692 | 14678 | 14558 |
| observed reflection | 219513 | 232493 | 271633 |
| 1/σ | 9 | 9 | 17 |

TABLE 3

X-ray crystallographic data from MAD method.

| Wave length (λ (Å)) | 0.979251 (edge) | 0.978815 (peak) | 0.971148 (remote1) | 0.986604 (remote2) |
|---|---|---|---|---|
| Resolution range (Å) | 20–2 | 20–2 | 20–2 | 20–2 |
| Measurements | 274641 | 219328 | 276044 | 271022 |
| Unique reflections | 14539 | 14566 | 14547 | 14539 |
| Completeness (%) | 99.6 (99.8) | 99.5 (98.5) | 99.6 (100) | 99.2 (84.7) |
| <I>/<σ(I)> | 19.6 | 19.6 | 19 | 19.3 |
| Rsym(I) (%) | 5.6 (15.1) | 5.7 (14.8) | 6.1 (16.7) | 5.3 (14.2) |
| Phasing statistics (20-2Å) | | | | |
| Mean figure of merit | | 0.7181 | | |
| Rcullis(dispersive) | — | 0.63 | 0.56 | 0.67 |
| Rcullis(anomalous) | 0.7 | 0.62 | 0.58 | 0.95 |
| Phasing power | — | 1.92 | 2.24 | 1.77 |
| Refinement statistics | | | | |
| Rcryst(Rfree) (%) | 23.8 (28.3) | | | |

TABLE 3-continued

X-ray crystallographic data from MAD method.

| | |
|---|---|
| rmsd bond length (Å) | 0.00641 |
| rmsd bond angles(°) | 1.11043 |
| rmsd impropers(°) | 0.70115 |

Figure 5:
FIG. 5 shows the three dimensional structures of Ras proteins prepared in vivo or by cell-free protein synthesis system displayed using computer graphics.
Figure 5:
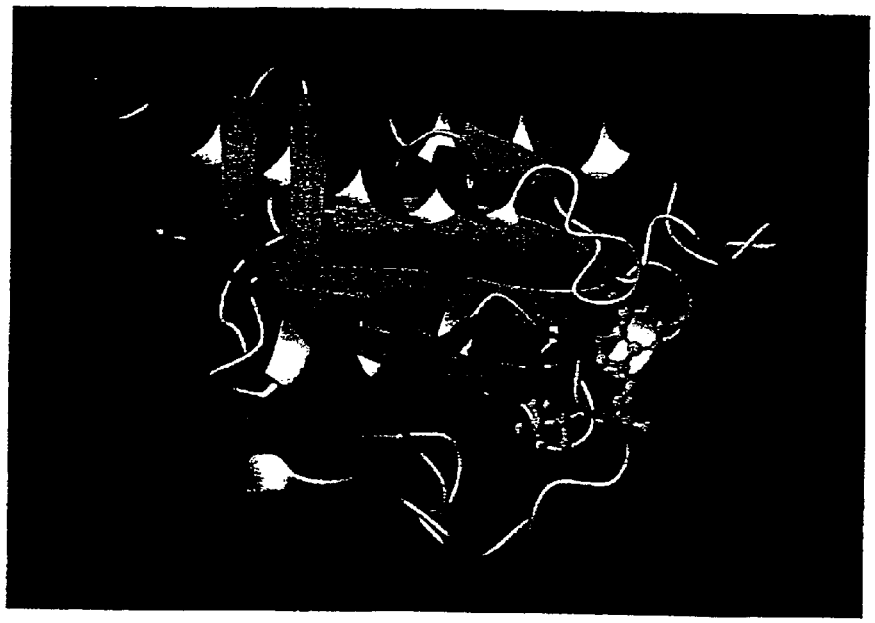

The model of the three dimensional structure of selenomethionine labeled Ras protein (Ras-GDP (Cell-free)) analyzed as mentioned above is shown in FIG. 5 in comparison with a model previously reported by deVos and his group (Ras-GDP (in vivo)). This figure shows that both of the three dimensional structures are almost the same.

The meritorious effects of the present invention are summarized as follows.

By the use of the methods of this invention, in comparison with existing protein synthetic methods which use living cells, it is possible to produce proteins comprising heavy atoms extremely easily and in great quantities. Produced proteins are ideally used to make the heavy atom replacement crystal suitable for X-ray crystallographic analyses, and this crystal makes efficient determinations of the three dimensional structures by the MAD method possible.

Through the development of such structural genomics research methods, high-throughput methods of structural analysis are established. And, the contributions to the lifesciences field made by the elucidation of functions through information about protein structure, such as the development of novel medicines, are expected.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

All references cited herein are hereby incorporated by reference in their entireties, whether previously specifically incorporated or not.

What is claimed is:

1. A method for producing a protein suitable for X-ray crystallographic analysis, comprising synthesizing a protein using a cell-free protein synthesis system comprising a cell extract, a nucleic acid coding for said protein, and amino acids for the substrate of said protein, wherein said amino acids comprise at least one amino acid comprising a heavy atom, and wherein said amino acid comprising the heavy atom is introduced into the synthesized protein at an introduced rate of at least 80%, thereby rendering the protein suitable for x-ray crystallographic analysis.

2. The method of claim 1, wherein said cell-free protein synthesis system further comprises a combination of creatine kinase and creatine phosphate as an adenosine triphosphate regenerating system.

3. The method of claim 1, wherein said heavy atom is any one selected from the group consisting of mercury, platinum, iodine, iron and selenium.

4. The method of claim 1, wherein said introduced rate of said amino acid comprising the heavy atom is at least 95%.

5. The method of claim 1, wherein said amino acid comprising the heavy atom is selenomethionine or selenocysteine.

6. The method of claim 5, wherein said introduced rate of said amino acid comprising the heavy atom is at least 95%.

7. The method of claim 1, wherein said cell-free protein synthesis system consists essentially of an internal dialysate and an external dialysate through a dialysis membrane, wherein said internal dialysate comprises said cell extract and said nucleic acid coding for asid protein, and wherein said amino acids for substrates of said protein comprising said internal dialysate and/or said external dialysate.

8. The method of claim 7, wherein said external dialysate further comprises an ATP regenerating system, a high-molecular weight absorbent and a reducing agent, and wherein said external dialysate is exchanged for a fresh dialysate when the rate of protein synthesis is reduced.

9. The method of claim 7, wherein the fractional molecular weight of said dialysis membrane ranges from 10,000 Da to 100,000 Da.

10. The method of claim 7, wherein said amino acid comprising the heavy atom is selenomethionine or selenocysteine.

11. The method of claim 1, wherein said cell extract is an extract of *Escherichia coli*, thermophilic bacteria or yeast.

12. The method of claim 11, wherein said amino acid comprising the heavy atom is selenomethionine or selenocysteine.

13. The method of claim 11, wherein said cell extract is a concentrated extract of *Escherichia coli* S30 cell extract fraction.

14. The method of claim 13, wherein said amino acid comprising the heavy atom is selenomethionine or selenocysteine.

* * * * *